United States Patent [19]

Wade et al.

[11] Patent Number: 5,130,227
[45] Date of Patent: Jul. 14, 1992

[54] RADIATION SENSITIVE PLATES

[75] Inventors: John R. Wade, Otley; Rodney M. Potts, Leeds; Michael J. Pratt, Menston, all of United Kingdom

[73] Assignee: Vickers Plc, London, United Kingdom

[21] Appl. No.: 418,758

[22] Filed: Oct. 5, 1989

Related U.S. Application Data

[63] Continuation of Ser. No. 191,831, May 9, 1988, abandoned, which is a continuation of Ser. No. 946,674, Dec. 31, 1986, abandoned, which is a continuation of Ser. No. 814,523, Dec. 19, 1985, abandoned, which is a continuation of Ser. No. 607,776, May 7, 1984, abandoned.

[30] Foreign Application Priority Data

May 9, 1983 [GB] United Kingdom ............... 8312721
May 9, 1983 [GB] United Kingdom ............... 8312722

[51] Int. Cl.$^5$ ............... G03F 7/029; G03F 7/031; G03F 7/033; C08F 2/50
[52] U.S. Cl. .................. 430/286; 430/281; 430/919; 430/920; 430/921; 430/922; 430/924; 430/926; 522/13; 522/15; 522/16; 522/24; 522/34; 522/48; 522/53; 522/60
[58] Field of Search ............ 522/13, 24; 430/286, 430/285, 281

[56] References Cited

U.S. PATENT DOCUMENTS

| | | | |
|---|---|---|---|
| 3,922,426 | 11/1975 | Feltzin | 522/13 |
| 4,008,084 | 2/1977 | Ikeda et al. | 430/278 |
| 4,048,036 | 9/1977 | Prucnal | 522/24 |
| 4,131,578 | 12/1978 | Fromson | 430/278 |
| 4,171,974 | 10/1979 | Golda et al. | 430/278 |
| 4,391,686 | 7/1983 | Miller | 522/13 |
| 4,416,826 | 11/1983 | Neckers | 544/106 |
| 4,498,963 | 2/1985 | Neckers | 430/923 |
| 4,500,629 | 2/1985 | Irving | 522/24 |
| 4,602,076 | 7/1986 | Ratclife | 522/13 |
| 4,604,295 | 8/1986 | Loctite | |
| 4,946,960 | 8/1990 | Wade | 548/150 |

FOREIGN PATENT DOCUMENTS 125140 11/1984 European Pat. Off. .
125875 11/1984 European Pat. Off. .
1062190 12/1983 U.S.S.R. .

OTHER PUBLICATIONS

Gupta "Photocrosslinking . . . " Chemical Abstracts vol. 96 No. 12, Abst. No. 860956, 1982.
Roffey, *Photopolymerization of Surface Coating*, Jun. 1982, John Wiley & Sons.

*Primary Examiner*—Marion E. McCamish
*Assistant Examiner*—Arthur H. Koeckert
*Attorney, Agent, or Firm*—Francis C. Hand

[57] ABSTRACT

A radiation sensitive plate comprises a substrate coated with a photopolymerizable composition. The composition comprises a polymerizable compound containing ethylenic unsaturation, a perester photoinitiator and optionally an optical sensitiser. The substrate may be a sheet of grained and anodized aluminum and the plate is useful in the production of lithographic printing plates.

8 Claims, No Drawings

RADIATION SENSITIVE PLATES

This application is a continuation of application Ser. No. 191,831, filed May 9, 1988, now abandoned, which is a continuation of application Ser. No. 946,674, filed Dec. 31, 1986 which is a continuation of Ser. No. 814,523 filed Dec. 19, 1985, now both abandoned, which is a continuation of application Ser. No. 607,776, filed May 7, 1984, now abandoned.

This invention relates to radiation sensitive plates for lithographic printing plate production.

Radiation sensitive plates are known comprising a radiation sensitive composition coated onto a substrate. Such radiation sensitive plates are used in lithographic printing plate production. It is also known to coat radiation sensitive compositions onto a substrate when using the compositions as photoresists.

In the use of radiation sensitive plates in lithographic printing plate production, the composition is image-wise exposed to actinic radiation so that parts of the composition are struck by radiation and parts are not. The composition is such that the radiation-struck parts and the non-radiation struck parts have different solubilities in a developer liquid. The image-wise exposed plate is then developed using the liquid so as to selectively remove the more soluble parts and leave an image constituted by the less soluble parts. The image constitutes the water repellent ink receptive printing area of the lithographic printing plate and the water receptive ink repellent non-printing area of the lithographic printing plate is constituted by the surface of the substrate revealed during the development step.

A wide variety of radiation sensitive compositions has been used to produce radiation sensitive plates. It is known to use, as the radiation sensitive composition, a polymerisable compound containing ethylenic unsaturation. In this case, on exposure to radiation the composition polymerises in those parts struck by the radiation and becomes less soluble in solvents for the non-radiation struck parts of the coating. Thus, the radiation sensitive plate is negative-working.

It is an object of the present invention to provide new radiation sensitive plates based on polymerisable compounds containing ethylenic unsaturation.

According to the present invention, there is provided a radiation sensitive plate comprising a substrate coated with a photopolymerisable composition comprising at least one polymerisable compound containing ethylenic unsaturation and a perester compound which, on exposure of the composition to radiation, initiates the polymerisation of said polymerisable compound.

On exposure to radiation, the peroxide linkage of the perester compound is cleaved to form free radicals which then cause the polymerisable material to polymerise.

In a first embodiment of the invention, the perester photoinitiator compound has the formula:

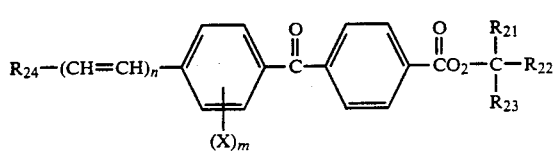

wherein $n = 0$ or 1; $m = 0$ or 1; $R_{24}$, when $n = 0$, represents hydrogen, optionally substituted alkyl or alkoxy, or a polymeric backbone;

$R_{24}$, when $n = 1$, represents hydrogen or optionally substituted alkyl; $R_{21}$, $R_{22}$ and $R_{23}$, which may be the same or different, each represents hydrogen, optionally substituted alkyl or optionally substituted aryl; and X represents optionally substituted alkyl or optionally substituted alkoxy.

Generally, in accordance with this embodiment, the composition includes an optical sensitiser, i.e. a material capable of broadening or altering the spectral response of the photopolymerisable composition so that it is responsive to the desired actinic radiation e.g. to the radiation emitted by an argon ion laser or to the radiation passing through the glass of a printing down frame having an ultra violet light source. Examples of suitable optical sensitisers are coumarins and bis-coumarins (GB Patent No. 1 578 662, U.S. Pat. No. 4,147,552 and published European Patent Application No. 221881); $\alpha,\beta$ unsaturated ketones (GB patent No. 1553 823, U.S. Pat. Nos. 3,652,275, 4,162,161 and 4,268,667 and GB published patent Application No. 2 006 775); methine dyes (GB patent No. 1 566 405, U.S. Pat. No. 2,732,301 and GB published patent Application No. 2 064 546); and pyrylium dyes (GB patents Nos. 1 023 377 and 1 566 405 and U.S. Pat. Nos. 3,907,561 and U.S. Defensive Publication No. 900,031).

Particularly preferred initiators in accordance with this first embodiment are:

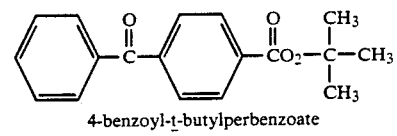

4-benzoyl-t-butylperbenzoate

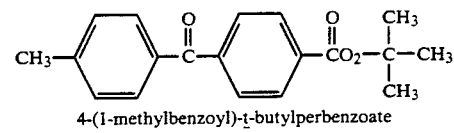

4-(1-methylbenzoyl)-t-butylperbenzoate

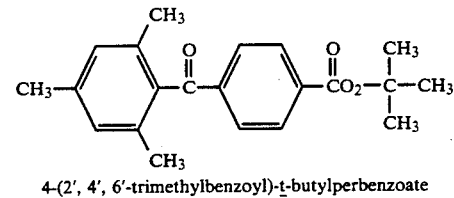

4-(2', 4', 6'-trimethylbenzoyl)-t-butylperbenzoate

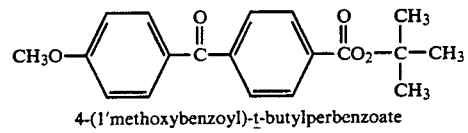

4-(1'methoxybenzoyl)-t-butylperbenzoate

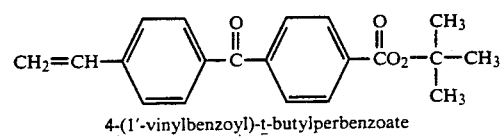

4-(1'-vinylbenzoyl)-t-butylperbenzoate

In accordance with a second embodiment of the invention, the perester photoinitiator compound has the general formula I

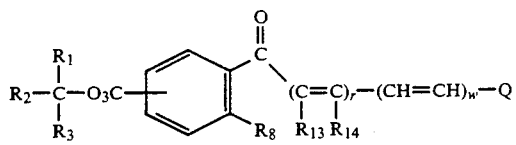

wherein
R₁, R₂ and R₃, which may be the same or different, represent H, optionally substituted alkyl or optionally substituted aryl;
r and w, which may be the same or different, equal 0 or 1;
Q, in the case where r and w both equal zero, represents (1b)

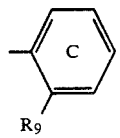

wherein R₈ and R₉, when taken together, represent —O—, —S—, >C=O, —CH— or a single bond and ring C is optionally substituted; Q, in the case where r=1, R₁₄ represents H, and R₈ and R₁₃ together represent the ring members necessary to complete an optionally substituted cycloalkan(di)one nucleus which may optionally include a hetero atom and may optionally be fused to an aromatic nucleus, represents (2b) an optionally substituted aromatic or heterocyclic radical, and Q, in the case where w=0, r=1. R₈ represents H, and R₁₃ represents H, acyl, heterocyclyl carbonyl, aroyl or

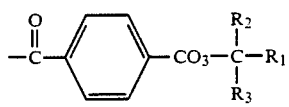

represents (3b)

wherein R₁₂ represents optionally substituted alkyl and R₁₅ and R₁₄, taken together, represent the ring members required to complete a 5- or 6-membered nitrogen containing ring which may be optionally fused to an optionally substituted aromatic nucleus.

In the case where the cycloalkan(di)one nucleus contains a hetero atom, this may be for example N, S, or O and in the case where the cycloalkane(di)one nucleus is substituted, the substituent(s) may be, for example OH, alkyl or aryl. In the case where ring C is alkoxy or N R₆R₇ where R₆ and R₇ have the meanings given hereinafter. The nitrogen containing heterocyclic ring formed by R₁₅ and R₁₄ is preferably quinoline, benzoxazole, benzothiazole, benzoselenazole, naphthothiazole, naphthoselenazole or benzo-2,3-dihydroindole.

Formulae 1 to 14 are typical perester photoinitiator compounds where Q represents (1b), formulae 15 to 24 are typical perester photoinitiator compounds where Q represents (2b), and formulae 25 to 50 are typical perester photoinitiator compounds where Q represents (3b).

In accordance with a third embodiment of the invention, the perester photoinitiator compound has the general formula II

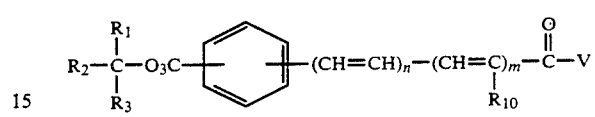

wherein
R₁, R₂ and R₃ have the above meanings;
m and n, which may be the same or different, equal 0 or 1;
R₁₀ represents H or optionally substituted alkyl; and
V represents either

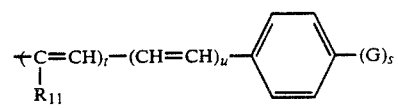

wherein
R₁₁ represents H, optionally substituted alkyl, or together with R₁₀ the ring members necessary to complete an optionally substituted cycloalkan(-di)one nucleus which may optionally include a hetero atom and may optionally be fused to an aromatic nucleus;
t, u and s, which may be the same or different equal 0 or 1 provided that m, n s, t and u are not all equal to O; and
G represents

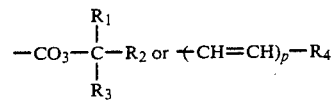

wherein
p equals 0, 1 or 2; and
R₄ represents
(1a) an optionally substituted aryl radical,
(2a) an optionally substituted hetero radical,
(3a)

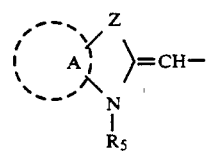

wherein
A represents an aromatic nucleus;
Z represents O,S or Se; and
R₅ represents H, optionally substituted alkyl or optionally substituted phenyl;
(4a) provided that m, n, t, u and p are all O,

wherein $R_6$ and $R_7$, which may be the same or different, represent H, optionally substituted alkyl, optionally substituted aryl, or an alkyl chain —$(CH_2I)_x$— where x is 2,3 or 4 covalently bonded to the adjacent ring, or (5al) provided that m, n, t u and p are not all zero, H, optionally substituted alkyl, optionally substituted alkoxy, optionally substituted phenoxy, a polymeric backbone, or N $R_6$ $R_7$ wherein $R_6$ and $R_7$ have the above meanings; or

(21) taken together with $R_{10}$, the ring members necessary to complete an optionally substituted cycloalkan(di)one ring nucleus which may optionally include a hetero atom and may optionally be fused to an aromatic nucleus.

In the case where the cycloalkan(di)one nucleus contains a heteroatom, this may be for example N, S or O and in the case where the cycloalkane(di)one nucleus is substituted, the substituent(s) may be, for example, OH, alkyl or aryl.

Formulae 51 to 96 are typical perester photoinitiator compounds in accordance with this third embodiment where, in the general formula V and $R_{10}$ together represent the ring members necessary to complete an optionally substituted cycloalkan(di)one ring nucleus which may optionally include a heteroatom and may optionally be fused to an aromatic nucleus.

The perester photoinitiator compounds used in accordance with these second and third embodiments form the subject matter of our copending Application of even date now U.S. Pat. No. 4,946,960.

The perester compounds may be prepared by conversion of appropriate carboxylic acids by two general methods:

1) Conversion of the acid to the corresponding acid chloride by reaction with thionyl chloride, followed by reaction of the isolated acid chloride with a hydroperoxide in the presence of triethylamine at a temperature below 5° C.

2) Conversion of the acid to the corresponding imidazolide by reaction with 1,1'-carbonyldiimidazolide. The imidazolide is then converted to the perester in situ by reaction with a hydroperoxide at a temperature below 5° C.

Appropriate carboxylic acid precursors may be prepared as follows:

Compounds of Formulae 1-4

Anthroquinone-2-carboxylic acids are prepared by conventional oxidation of corresponding 2-methylanthroquinone as described by Whitmore and Carnalon (Journal of the American Chemical Society 958, 51, 1929).

Compounds of Formulae 5-7

Suitable acids (fluorenone-2- and fluorenone-4-carboxylic acids) are available commercially from Aldrich or may be prepared (fluoroenone-3-carboxylic acid) by the method described in Kruber (Ber, 1382,65, 1932).

Compounds of Formulae 8-14

Suitable thioxanthone and xanthone carboxylic acid may be prepared by the methods described in GB Patent Specification No.2 050 378.

Compounds of Formulae 15-24

Suitable precursors may be prepared by reacting carboxy aryl ketones with arylaldehydes by the methods described in U.S. Pat. No. 4,162,162. The carboxy arylketones may be prepared by the methods described by Allinger and Jones (Journal of Organic Chemistry 70,27, 1962).

Compounds 25-50

These compounds may be prepared by methods illustrated by the following typical examples:

A) Preparation of the Compound of Formulae 25

To an ice-cooled solution of terephthaloyl chloride (2.33g) in toluene (60ml) was added a solution of t-butylhydroperoxide (1.29g of 80%) and triethylamine (1.22g) in 1:1 diethylether/toluene (30ml), dropwise over 1 hour. The temperature of the stirred solution was maintained below 5 deg. C. during the addition.

1,2-dimethylbenzothiazolium p-toluene sulphonate (3.35g) was added to the above solution, followed by a solution of triethylamine (2.33g) in toluene (15ml) dropwise over a half hour at 10°-15 deg C. The reaction mixture was stirred for 2 hours at room temperature and then filtered. The filtrates were extracted with dilute hydrochloric acid (approx. 1M), washed with water and dried over anhydrous magnesium sulphate. Solid product was isolated after the removal of excess solvent from the dried extracts on a rotary evaporator. Recrystallization of this material in ethyl acetate gave (1.4g), m.p. 160 deg C. (decomp.).

B) Preparation of the Compound of Formula 27

4-t-Butylperoxycarbonylbenzoyl chloride (BPCBC) was, prepared as described in the first paragraph of (A). The product was isolated as a colourless oil which slowly solidified when stored in the refrigerator after solvent had been evaporated from the filtrate of the reaction mixture.

A mixture of 1,2-dimethylbenzo-selenazolium-p-tosylate (1.78g) , BPCBC (2.75g) and dry pyridine(10 ml) was heated on a steam bath for 2 hours. The resultant mixture was diluted to a volume of 100ml with toluene, stirred and the solution was separated from a tarry residue which had formed. The toluene solution was washed with water and then dried over magnesium sulphate.

The product was isolated after the removal of excess solvent from the dried solution on the rotary evaporator. Recrystallisation of this material in ethyl acetate gave a product having a melting point of 120° C. (decomposes).

C) Preparation of the Compound of Formula 40

To a stirred solution of 1,3,3-trimethyl-2 methyleneindoline (3.6ml) in dry toluene (20ml) was added, dropwise, a solution of BPCBC (6.1 g) in dry toluene (15 ml). When the addition was complete, the mixture was heated to 60 ° C. and maintained at this temperature for 1½ hours before filtering. After cooling to room temperature the toluene solution was extracted with base and washed with water before drying over magnesium sulphate. A red solid was obtained from the toluene solution after removal of solvent on a rotary evaporator. Recrystallisation of this material in chloroform/methanol gave a product having a melting point of 76° C. (decomposes).

Compounds of Formulae 51-90

Suitable carboxylic acid precursors may be prepared by base catalysed condensation of arylaldehydes with cycloalkanones or aryl ketones as illustrated by the following preparations.

2-(4'-carboxyl) benzylideneindan-1-one

Indan-1-one (1.32 g) and 4-carboxylbenzaldehyde (1.50g) were added to ethanol (15ml). The resultant mixture was heated to reflux before adding a 10% w/v aqueous solution of sodium hydroxide (15ml). Refluxing was continued for 1 hour. On cooling, the reaction mixture was drowned out into 1M hydrochloric acid (25ml) to yield a white solid which was collected at the pump, washed acid free with water and dried. The yield of product was 2.54g , m.p. 208°-211 deg C. (decomp.).

4-(4'-Dimethylaminocinnamoyl) Benzoic Acid

4-Acetylbenzoic acid (1.5g) and 4-dimethylaminobenzaldehyde (1.38g) were warmed in 10% aqueous caustic soda (35 ml) until dissolved. The solution was allowed to cool, with stirring. An oil was formed which crystallised to give a red-brown solid (sodium salt) which was filtered off and converted to the acid with warm 1M acetic acid. The product was recrystallised from ethanol and had a melting point of 246°-249° C.

Compounds of Formulae 91-96

These compounds may be prepared from the triphenyl phosphonium salt of 4-(4'-bromomethyl-benzoyl) methylbenzoate, which may be prepared by the procedure described by Gupta et al (Journal Polymer Science 855 19 1981). The procedures to convert the phosphonium salt through to the final product are illustrated by the following examples.

Preparation of the Compound of Formula 92 i) Preparation of 4-(4'-Benzylidenebenzoyl) Methyl Benzoate

To an ice-cooled solution of the triphenylphosphonium salt of 4-(4'-bromomethylbenzoyl) methylbenzoate (17.85g) in methanol (100ml) was added, dropwise, a solution of sodium methoxide (1.62g) in methanol (40ml), followed by benzaldehyde (3.3g). A pink precipitate was formed. Stirring was continued for ½ hour at room temperature before the precipitate was collected and washed. Several further crops were obtained from the filtrates. The product was recrystallised from chloroform.

ii) Preparation of 4-(4'-Benzylidenebenzoyl) Benzoic Acid

To a dispersion of 4-(4'-benzylidenebenzoyl) methyl benzoate (4.07g) in toluene (120ml) was added a solution of potassium hydroxide (0.9g) in methanol (20ml). The resultant mixture was stirred for 72 hours at room temperature . The resulting suspension was extracted several times with water and the aqueous portions were combined, filtered and acidified with 1M H$_2$SO$_4$.

iii Conversion of the Benzoic Acid

To an ice cooled solution of 4-(4'-benzylidene benzoyl)-benzoic acid (1.40g) in THF was added a solution of 1,1'-carbonyldiimidazole (0.7g) in THF (10ml), with stirring. After 2 hours, a solution of t-butylhydroperoxide (0.5g of 80%) in THF (10ml) was added slowly. Stirring was continued for a further hour at 0° C. after which the solution was filtered and the solvent removed. The resulting oil was purified by column chromatography (silica) using dichloromethane as eluant. The resultant colourless oil solidified on overnight refrigeration to give a product having a melting point of 72°-76° C.

Generally, in accordance with the second and third embodiments, optical sensitisers do not need to be included in the radiation sensitive composition. However when present, the sensitiser together with the perester photoinitiator compound, may constitute up to about 20% of the total weight of the composition. The optimum content of the sensitiser is about 5% by weight of the composition. Similarly, the perester photoinitiator compound is optionally present in an amount of about 5%.

Any addition polymerisable compound containing ethylenic unsaturation can be used in the photopolymerisable composition of the radiation sensitive plate of the present invention. Preferred are simple compounds, or monomers as they are sometimes denominated, containing ethylenic unsaturation, as well as polymers containing end groups or pendant groups terminating with ethylenic unsaturation. For example, the phrase "addition polymerisable compound" is intended to include polymers having recurring units with the structure

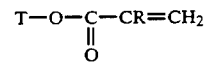

wherein T is any group capable of forming the backbone of a polymer and R is hydrogen or methyl.

Other examples of useful addition polymerisable compounds containing ethylenic unsaturation include monomeric (meth)acrylates, (meth)acrylamides, allyl compounds, vinyl ethers, vinyl esters, N-vinyl compounds, styrenes, acrylonitriles and crotonates. Many examples of each of these classes are well known, such as those listed, for example, in GB Patent No. 1 534 137.

A highly preferred class of addition polymerisable compounds encompasses the (meth)acrylate compounds. Particularly useful examples include alkyl (meth)acrylates containing from 1 to 30 and most preferably 1 to 5 carbon atoms in the alkyl portion, such as methyl and ethyl (meth)acrylates; pentaerythritol tri- and tetra (meth)acrylates; esters of polyols, including glycol di(meth)acrylates, such as tripropylene glycol diacrylate, tetraethylene glycol diacrylate and triethylene glycol dimethacrylate; alkanediol di(meth) acrylates; urethane (meth)acrylates such as the reaction products of hydroxyl group containing (meth)acrylates with di or poly isocyanates; epoxy (meth)acrylates; and mixtures of the above.

The addition to the photopolymerisable composition of a polymeric binder is desirable to strengthen the composition and improve the adherence of the composition to the substrate. Typical binders are acrylic polymers, vinyl acetate polymers, and novolak resins. Many examples of suitable polymers are listed in the patent literature and reference may be made for example, to U.S. Pat. Nos. 3,652,275 and 4,268,667 and GB published Patent Application No. 2 006 The binder 4 775.1 may be present in an amount up to the amount of the polymerisable compound.

As is well known, the polymerisation of vinyl group containing monomers is inhibited by the presence of oxygen. It is therefore desirable to provide, over the photopolymerisable composition coating, a barrier layer which is transparent to radiation and also impervious to oxygen. A layer of polyvinyl alcohol is particularly suitable for this purpose.

The substrate may be any substrate conventionally used with photo resists or in the production of lithographic printing plates and a substrate formed of grained and anodised aluminium is particularly preferred.

The following Examples illustrate the invention.

EXAMPLE 1

A solution in ethyl methyl ketone of a photopolymerisable composition comprising:

3 parts by weight of the dimethacrylate ester of diglycidyl ether of bisphenol A, 1 part by weight of a vinyl acetate/crotonic acid copolymer, 0.15 parts by weight 4-(2', 4', 6'-trimethyl benzoyl)-t-butyl perbenzoate and 0.15 weight of Ethyl Michler's Ketone, was whirler coated onto a sheet of electrochemically grained and anodised aluminium and dried to form a radiation sensitive plate. The coating weight was 1 g per sq. m.

The dried coating was overcoated with poly(vinyl alcohol) to prevent oxygen inhibition.

The radiation sensitive plate was exposed through a continuous tone Stouffer step-wedge to ultra violet light (¼ unit from a Berkey-Ascor printing down frame) and then developed with an aqueous solution containing sodium propanoate, sodium benzoate and a surfactant. The developed image of the resultant lithographic printing plate had a step-wedge of solid 3, tail 7.

When placed on a printing press, the printing plate produced many satisfactory copies.

EXAMPLE 2

Example 1 was repeated using the four alternative optical sensitisers listed below and the developed images of the resultant printing plates had the step-wedge readings shown:

| Sensitiser | Solid/Tail |
| --- | --- |
| 2-Benzoylmethylene-3-methylnaphthothiazoline | 4, 9 |
| 2-Dibenzoylmethylene-3-methylbenzoselenazoline | 2, 7 |
| 7-Diethylamino-4-methyl-coumarin | 3, 7 |
| 3-Carboethoxy-7-diethylamino-coumarin | 2, 7 |

When placed on a printing press, the printing plates produced many satisfactory copies.

EXAMPLE 3

Example 1 was repeated using 4(1'methoxybenzoyl)-t-butyl perbenzoate as the initiator. Similar results were obtained except that the radiation sensitive plate was more sensitive, producing a solid 5, tail 9 step wedge on development.

EXAMPLE 4

Example 1 was repeated except that the Ethyl Michler's Ketone was replaced by 0.15 parts by weight of 2,6-bis(4'-diethylaminobenzylidene)cyclohexanone as optical sensitiser and the plate was exposed for 20 seconds to light from a xenon arc through a Wratten 45 filter which transmits light in the range 440–540 nm. The developed image had a step wedge of solid 5, tail 13. When this sensitiser was omitted from the coating, the resultant plate gave no image when exposed under similar circumstances.

EXAMPLE 5

Example 4 was repeated using t-benzoyl-t-butylperbenzoate as the initiator and the four alternative optical sensitisers listed below. The developed images had the step-wedge readings shown:

| Sensitiser | Solid/Tail |
| --- | --- |
| 3,3'-Diethyloxacarbocyanine iodide | 6, 15 |
| 3,3'-Diethyl-9-methyloxacarbocyanine iodide | 3, 10 |
| 3,3',9-Triethyloxacarbocyanine iodide | 4, 13 |
| 3,3'-Carbonylbis(7-diethyl-amino coumarin | 4, 12 |

EXAMPLE 6

A piece of electrochemically grained and anodised aluminium was whirler coated with a solution in ethyl methyl Ketone of a photopolymerisable composition comprising:

3 parts by weight of the dimethacrylate ester of Example 1, 0.15 parts by weight of Ethyl Michler's Ketone, and 0.15 parts by weight of the perester initiator of Example 1.

No oxygen inhibiting layer was applied. The resultant radiation sensitive plate was exposed beneath a Stouffer step-wedge on a Laserite 65R laser exposure unit (EOCOM Corporation) with an Argon ion laser emitting at 351.1 nm and 363.8nm. The exposure energy was 2mJcm$^{-2}$. After development as in Example 1, a step-wedge reading of solid 2, tail 9 was obtained.

EXAMPLE 7

Example 1 was repeated twice using an aromatic urethane acrylate (EBECRYL 210) and a polyester acrylate (EBECRYL 810) as the polymerisable compound. (EBECRYL is a Trade Mark of ucb s.a. of Drogenbus, Belgium). Similar results were obtained.

EXAMPLE 8

To compare the properties of the compounds of formulae 1 to 96, Example 1 was repeated using radiation sensitive plates made in accordance with Example 1 but with the initiator replaced by compounds 1 to 96. The results obtained in each case are shown in the following Table which also indicates the optical sensitiser (if used) and the exposure conditions.

The optical sensitisers indicated in the table are as follows:

EMK = Ethyl Michlers Ketone

BNTZ = 2 -Benzoylmethylene-3-methylnaphthothiazoline

DOCl = 3,3'-Diethyloxacarbocyanine iodide.

The exposure conditions were:
A = ½ unit on Berkey-Ascor frame
B = 20 seconds to Xe arc through Wratten 45 filter (transmission 440-540 nm)
C = 20 seconds to Xe arc through Wratten 47 filter (transmission 400-500 mm).

All the exposures were made through a Stouffer step-wedge. The absorbance given is the wavelength of the longest radiation having an absorbance peak.

TABLE

| Initiator Formula | Optical Sensitiser | Exposure | Step Wedge Solid Tail | Absorbance (nm) |
|---|---|---|---|---|
| 1 | EMH | A | 3, 9 | 324 |
| 2 | " | " | 3, 9 | 323 |
| 3 | " | " | 2, 8 | 328 |
| 3 | DOC 1 | B | 3, 9 | |
| 4 | " | B | 1, 7 | 396 |
| 5 | EMH | A | 4, 9 | 352 |
| 6 | " | " | 0, 5 | 343 |
| 7 | " | " | 0, 4 | 345 |
| 8 | " | " | 3, 8 | 350 |
| 9 | NONE | " | 4, 10 | 396 |
| 10 | " | " | 5, 12 | 404 |
| 11 | " | " | 6, 12 | 418 |
| 12 | " | " | 8, 13 | 400 |
| 13 | " | " | 0, 7 | 388 |
| 14 | " | " | 1, 8 | 406 |
| 15 | " | C | 6, 12 | 441 |
| 16 | " | " | 7, 13 | 432 |
| 17 | " | " | 7, 12 | 465 |
| 18 | " | " | 2, 7 | 486 |
| 19 | " | " | 8, 13 | 451 |
| 20 | " | " | 9, 14 | 462 |
| 21 | " | " | 4, 10 | 439 |
| 22 | " | " | 2, 7 | 422 |
| 23 | " | " | 3, 7 | 440 |
| 24 | " | " | 7, 12 | 433 |
| 25 | " | A | 10, 14 | 397 |
| 26 | " | " | 4, 9 | 396 |
| 27 | " | " | 2, 5 | 394 |
| 28 | " | " | 12, 18 | 401 |
| 29 | " | A(5 units) | 2, 5 | 373 |
| 30 | " | A | 9, 13 | 395 |
| 31 | " | " | 3, 8 | 392 |
| 32 | NONE | A | 8, 13 | 404 |
| 33 | " | A | 4, 9 | 378 |
| 34 | " | " | 5, 11 | 385 |
| 35 | " | " | 3, 7 | 382 |
| 36 | " | " | 9, 13 | 397 |
| 37 | " | " | 11, 16 | 398 |
| 38 | " | " | 8, 14 | 406 |
| 39 | " | " | 3, 9 | 380 |
| 40 | " | " | 10, 14 | 395 |
| 41 | " | " | 11, 15 | 395 |
| 42 | " | " | 2, 8 | 417 |
| 43 | " | " | 3, 7 | 398 |
| 44 | " | " | 3, 7 | 397 |
| 45 | " | " | 9, 14 | 409 |
| 46 | " | " | 7, 13 | 407 |
| 47 | " | " | 2, 7 | 398 |
| 48 | " | " | 2, 6 | 372 |
| 49 | " | " | 5, 11 | 395 |
| 50 | " | " | 0, 5 | 404 |
| 51 | BNTZ | " | 5, 11 | 304 |
| 52 | " | " | 1, 8 | 312 |
| 53 | " | " | 0, 5 | 300 |
| 54 | " | " | 2, 7 | 340 |
| 55 | " | " | 2, 8 | 298 |
| 56 | " | " | 3, 9 | 301 |
| 57 | " | " | 1, 7 | 296 |
| 58 | " | " | 2, 9 | 311 |
| 59 | " | " | 4, 11 | 299 |
| 60 | " | " | 6, 12 | 378 |
| 60 | NONE | " | 3, 9 | 378 |
| 62 | BNTZ | " | 4, 11 | 311 |
| 62 | " | " | 1, 6 | 315 |
| 63 | BNTZ | A | 1, 7 | 323 |
| 64 | " | " | 1, 7 | 303 |
| 65 | " | " | 4, 11 | 321 |
| 66 | " | " | 3, 8 | 304 |
| 67 | " | " | 1, 6 | 301 |
| 68 | " | " | 3, 8 | 308 |
| 69 | " | " | 5, 10 | 314 |
| 70 | " | " | 2, 7 | 288 |
| 71 | " | " | 2, 8 | 298 |
| 72 | " | " | 4, 11 | 312 |
| 73 | " | " | 1, 7 | 341 |
| 74 | " | " | 2, 8 | 306 |
| 75 | " | " | 2, 8 | 311 |
| 76 | " | " | 4, 11 | 313 |
| 77 | " | " | 0, 6 | 322 |
| 78 | " | " | 0, 5 | 311 |
| 79 | NONE | B | 2, 7 | 443 |
| 80 | NONE | A | 3, 8 | 406 |
| 81 | " | | 3, 9 | 364 |
| 81 | EMK | | 6, 11 | 364 |
| 82 | " | " | 3, 9 | 308 |
| 83 | " | " | 1, 7 | 300 |
| 84 | NONE | " | 2, 8 | 402 |
| 85 | " | " | 4, 11 | 400 |
| 86 | " | B | 2, 9 | 425 |
| 87 | " | " | 5, 12 | 448 |
| 88 | " | " | 3, 10 | 477 |
| 89 | EMK | A | 4, 10 | 328 |
| 90 | NONE | " | 3, 9 | 386 |
| 91 | EMK | " | 6, 12 | 308 |
| 92 | " | " | 5, 9 | 312 |
| 93 | " | " | 3, 8 | 341 |
| 94 | NONE | A | 5, 10 | 400 |
| 94 | " | B | 7, 12 | 400 |
| 95 | " | A | 6, 11 | 412 |
| 95 | " | B | 9, 14 | 412 |
| 96 | " | A | 4, 10 | 428 |
| 96 | " | B | 8, 13 | 428 |

EXAMPLE 9

Example 1 was repeated except that the amount of the initiator was increased to 0.3 parts by weight. The developed image had a step wedge of solid 12, tail 16.

EXAMPLE 10

A solution in ethyl methyl ketone of a photopolymerisable composition comprising:

3 parts by weight of the dimethacrylate ester of diglycidyl ether of bisphenol A, 1 part by weight of a vinyl acetate/crotonic acid copolymer, and 0.15 pts by weight of the photo initiator of formula (25) was whirler coated onto a sheet of grained and anodised aluminium and dried to form a radiation sensitive plate. The coating weight was 1 $g.m.^{-2}$.

The dried coating was overcoated with poly(vinyl alcohol) to prevent oxygen inhibition.

The radiation sensitive plate was exposed through a continuous tone Stouffer step-wedge to ultra violet light (0.03 unit) from a Berkey-Ascor printing down frame and developed with an aqueous solution containing sodium propanoate, sodium benzoate and a surfactant. The developed image of the resultant lithographic printing plate had a step-wedge of solid 10 tail 14.

EXAMPLE 11

Example 10 was repeated except that the solution also contained 0.15 parts by weight of Ethyl Michler's Ketone as optical sensitiser. The developed image had a step-wedge of solid 11 tail 18.

EXAMPLE 12

Examples 10 and 11 were repeated using the photo initiator of formula 26.

Similar results to those of Examples 10 and 11 were obtained.

EXAMPLE 13

A piece of grained and anodised aluminium was whirler coated to a weight of 1 g.m.$^{-2}$ with a solution in ethyl methyl ketone of a photopolymerisable composition comprising 3 parts by weight of the monomer of Example 10, 1 part by weight of phthaloylated poly(vinyl butyral), and 0.15 parts by weight of the initiator of formula 94.

The resultant radiation sensitive plate was exposed through a Stouffer step-wedge for 20 seconds to light from a xenon arc through a Wratter 45 filter which transmits light in the range 440–540 nm. The developed image of the resultant lithographic printing plate had a step-wedge of solid 9, tail 14.

EXAMPLE 14

Example 13 was repeated except that the radiation sensitive plate was exposed using a Laserite 65R laser exposure unit (EOCOM Corporation) with an Argon ion laser emitting at 488 nm. The exposure energy was 5 mJcm$^{-2}$. After development a step-wedge reading of solid 3, tail 8 was obtained.

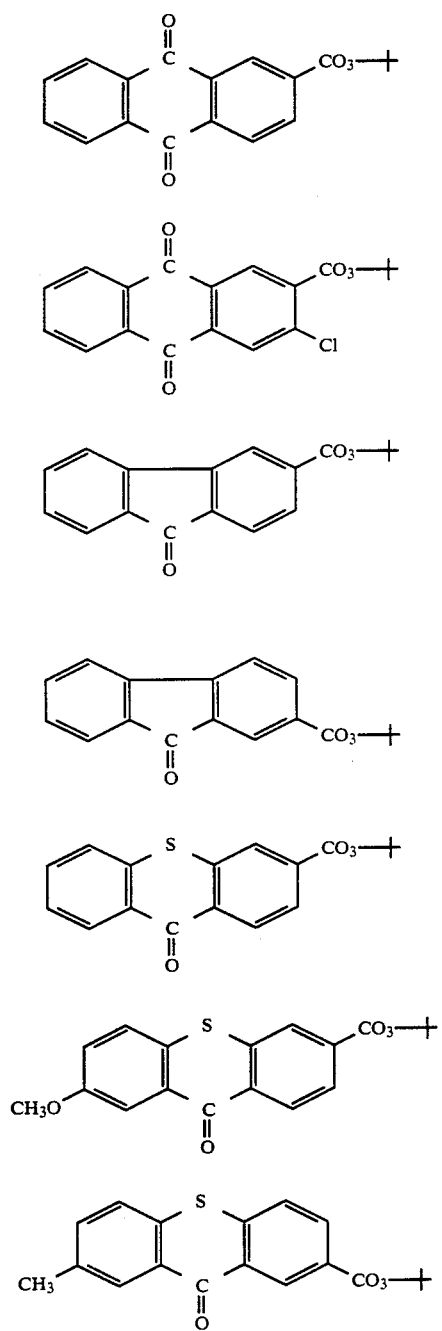

-continued
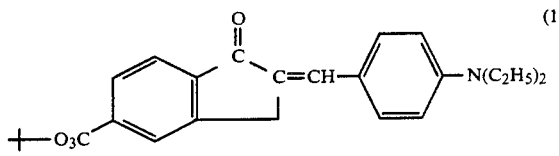 (15)
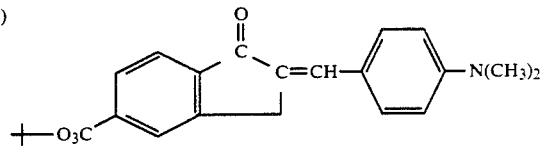 (16)
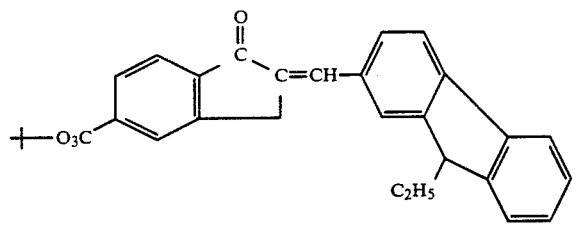 (17)
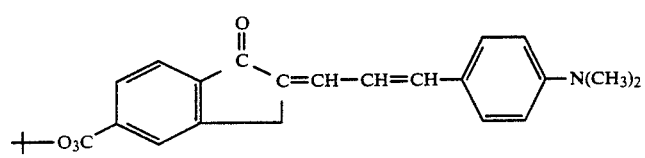 (18)
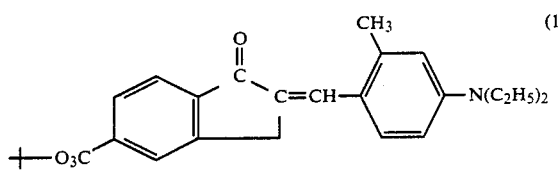 (19)
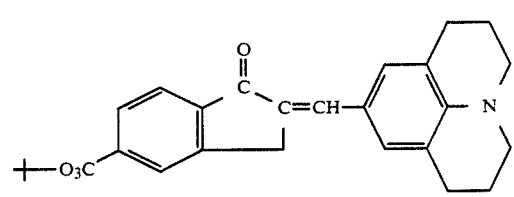 (20)
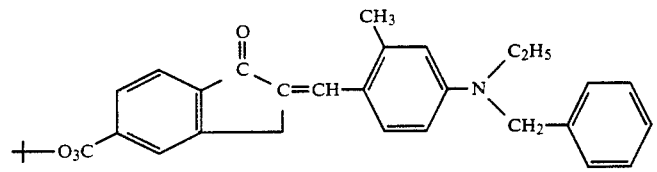 (21)
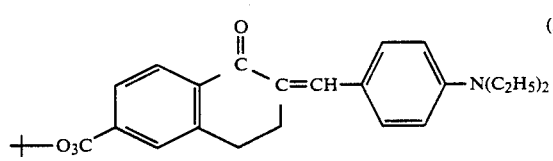 (22)
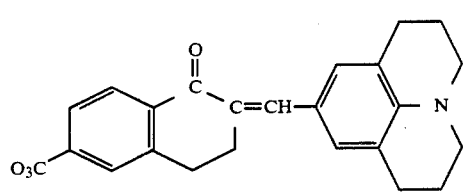 (23)
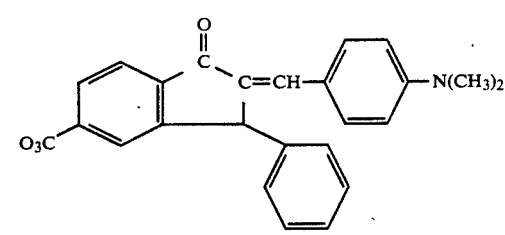 (24)
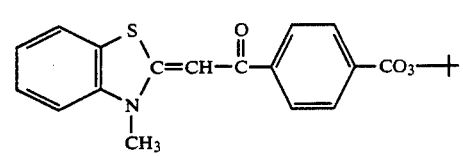 (25)
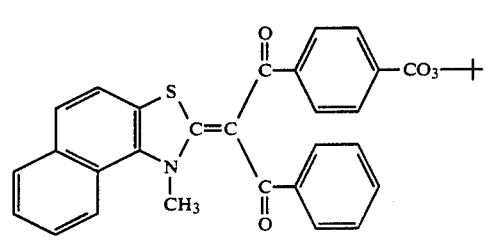 (26)
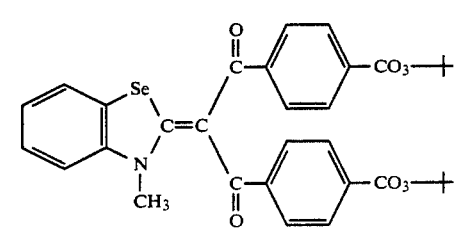 (27)

-continued
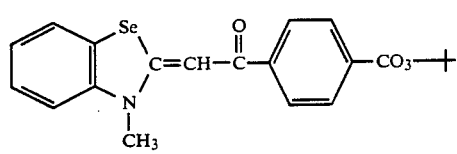 (28)
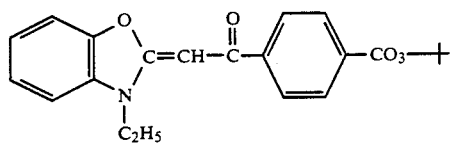 (29)
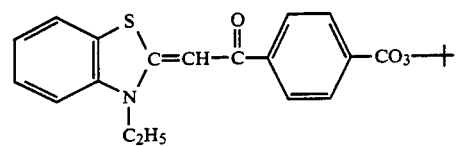 (30)
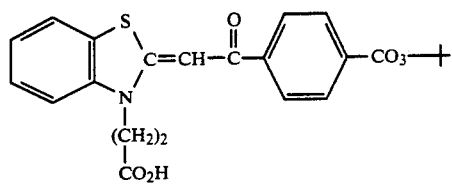 (31)
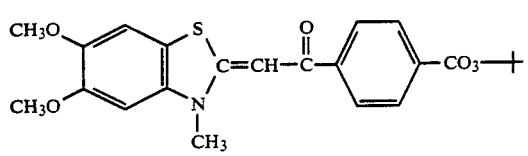 (32)
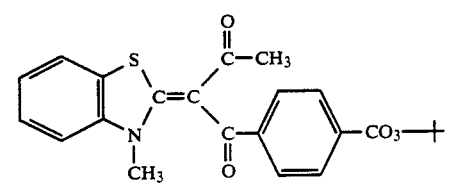 (33)
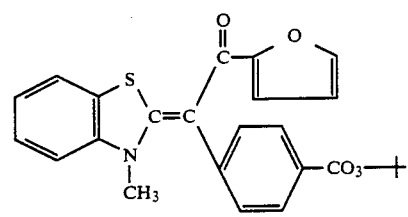 (34)
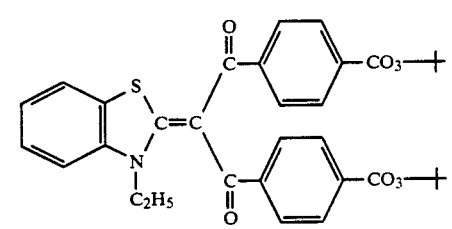 (35)
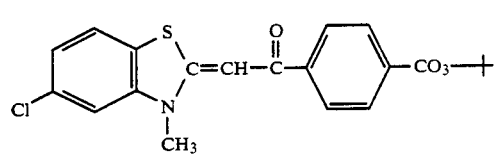 (36)
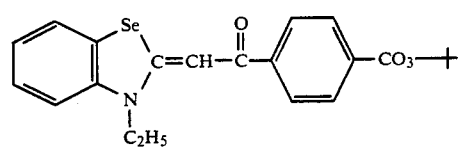 (37)
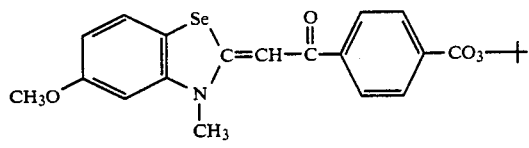 (38)
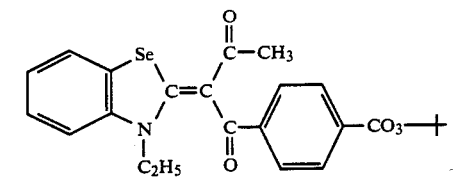 (39)
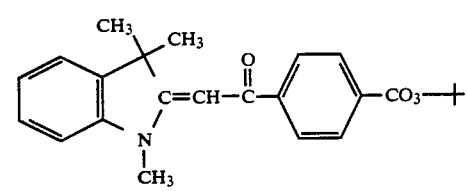 (40)
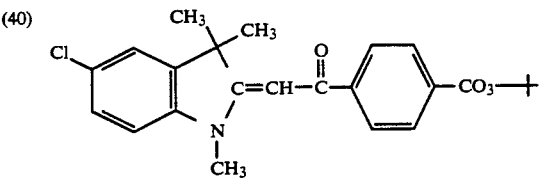 (41)
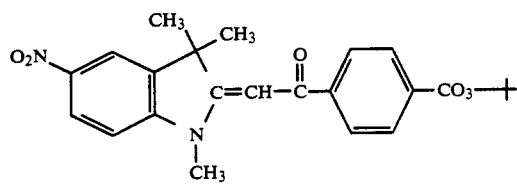 (42)
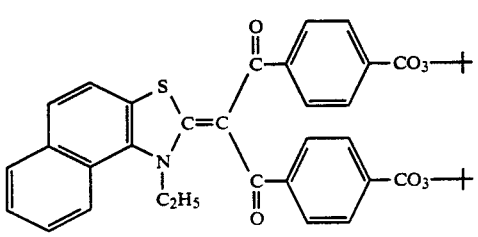 (43)

-continued
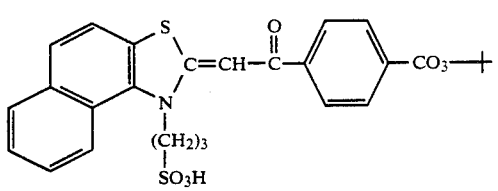 (44)
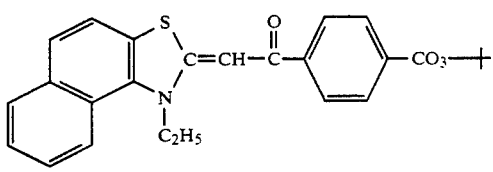 (45)
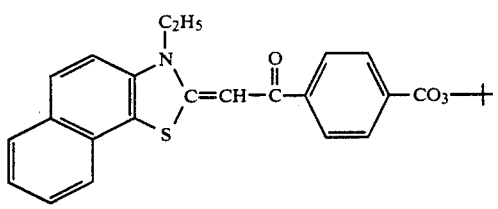 (46)
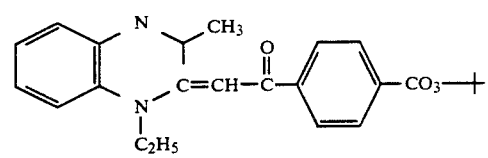 (47)
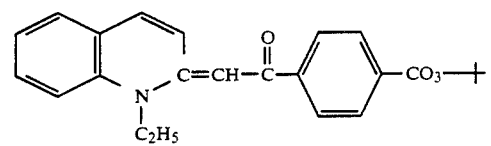 (48)
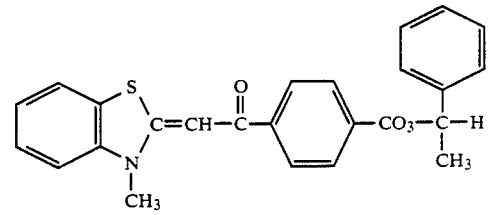 (49)
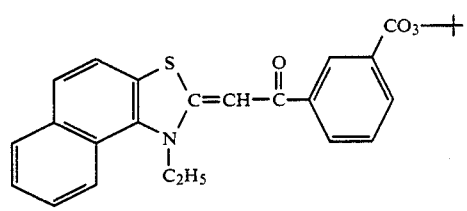 (50)
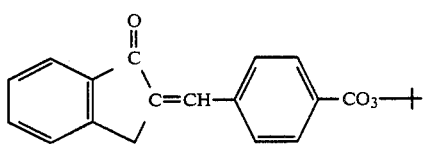 (51)
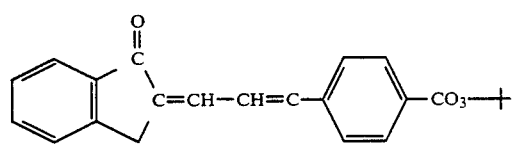 (52)
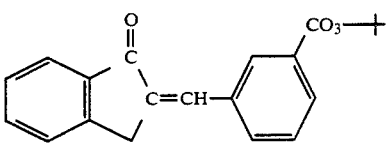 (53)
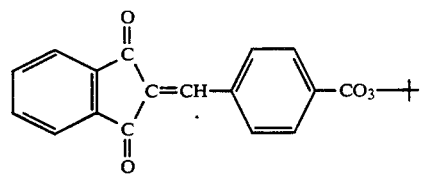 (54)
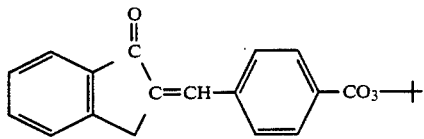 (55)
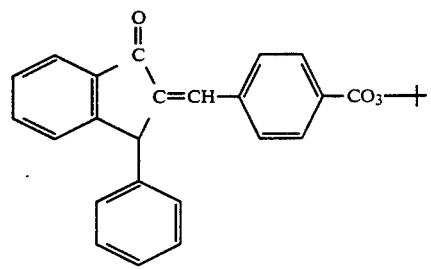 (56)
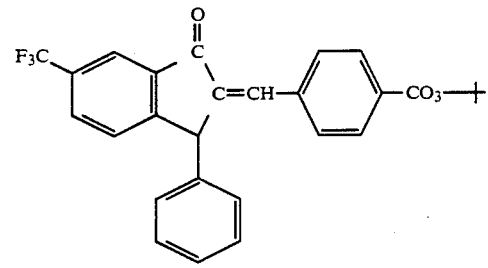 (57)

-continued
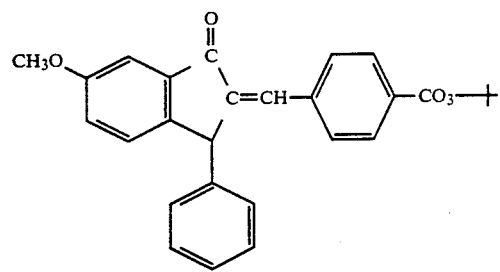 (58)
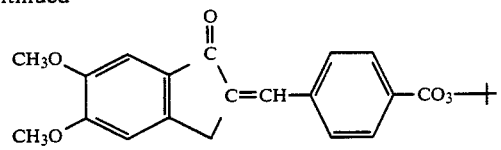 (59)
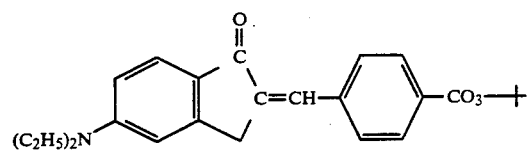 (60)
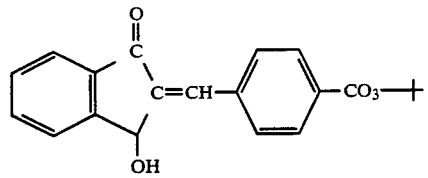 (61)
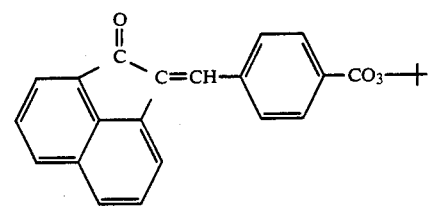 (62)
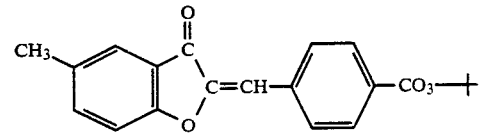 (63)
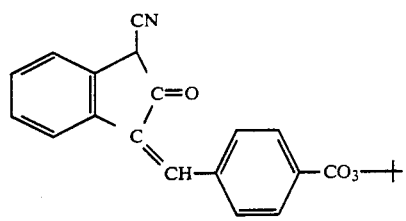 (64)
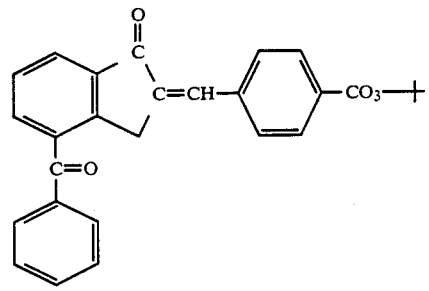 (65)
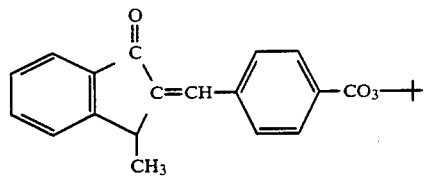 (66)
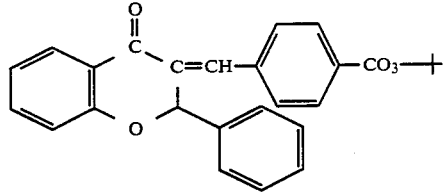 (67)
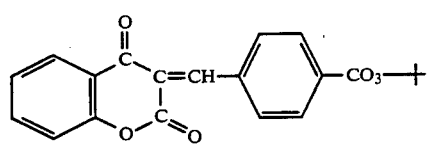 (68)
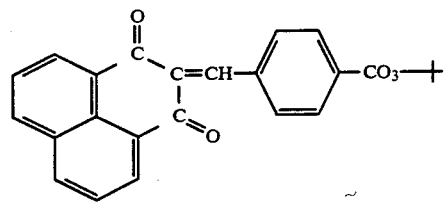 (69)
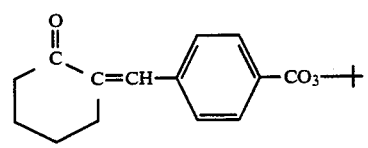 (70)
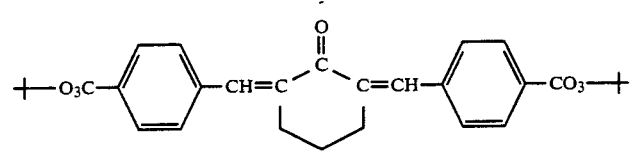 (71)

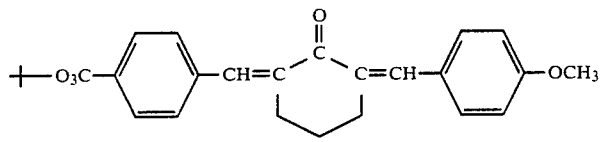
(72)
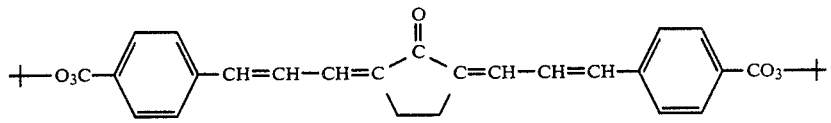
(73)
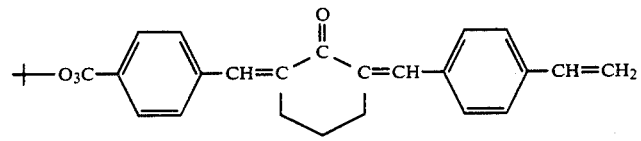
(74)
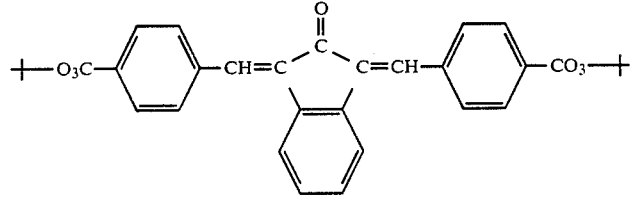
(75)
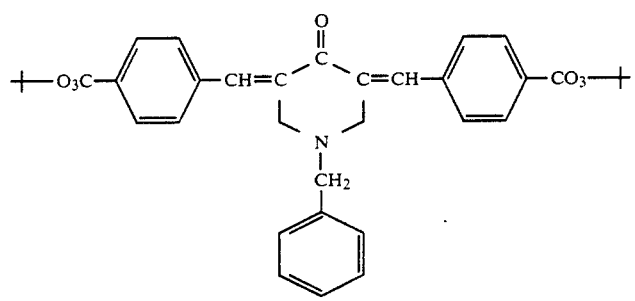
(76)
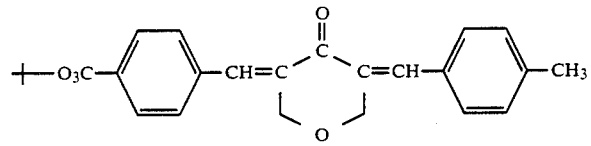
(77)
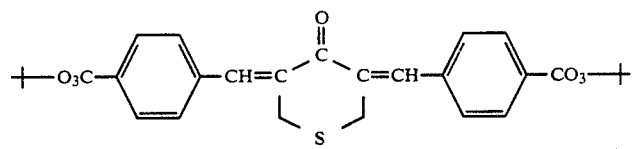
(78)
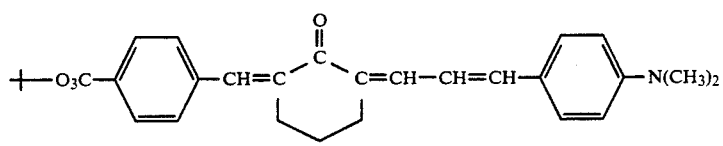
(79)
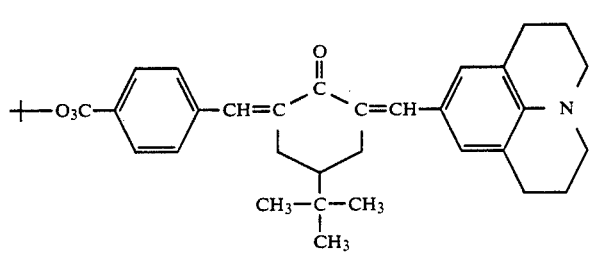
(80)

-continued

(81) 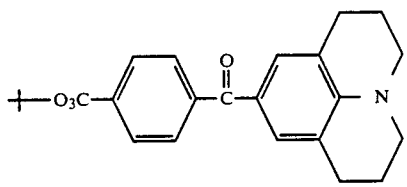

(82) 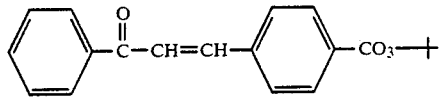

(83) 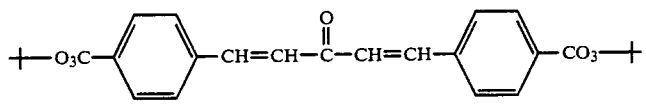

(84) 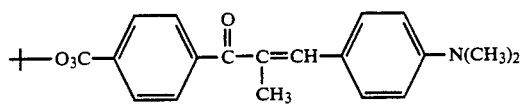

(85) 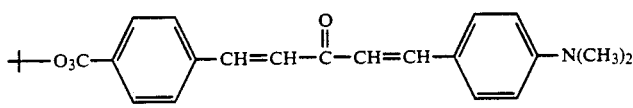

(86) 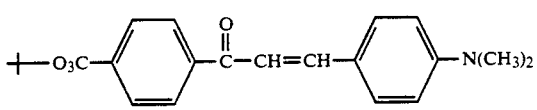

(92) 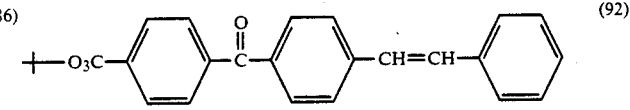

(93) 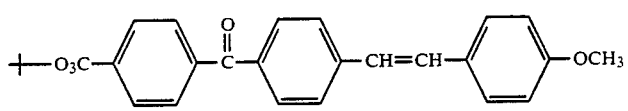

(94) 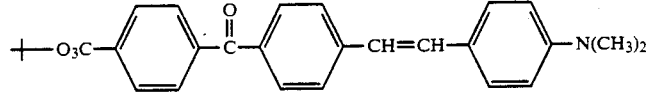

(95) 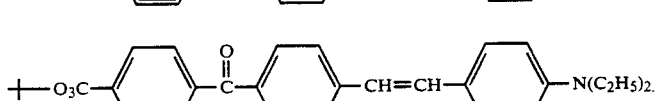

(96) 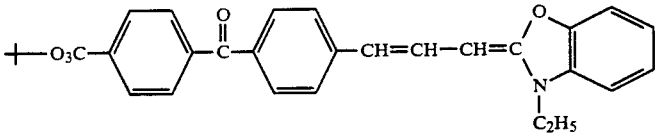

We claim:
1. A radiation sensitive plate comprising a substrate coated with a photopolymerizable composition comprising (i) at least one polymerizable compound containing ethylenic unsaturation; and (ii) a perester compound having the general formula:

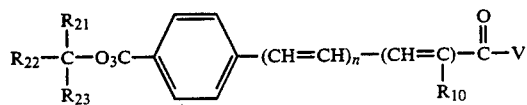

wherein
$R_{21}$, $R_{22}$ and $R_{23}$ are each selected from the group consisting of hydrogen, an alkyl radical and an aryl radical;

n equals 0 or 1, and $R_{10}$ is selected from the group consisting of hydrogen or an alkyl radical, and V is selected from the group consisting of an aryl radical and a radical which taken with $R_{10}$ forms a ring structure including an aryl radical conjugation with the carbonyl; and (iii) optical sensitizer.

2. The radiation sensitive plate as claimed in claim 1, wherein the optical sensitizer is selected from the group consisting of coumarins, bis-coumarins, $\alpha,\beta$-unsaturated ketones, methine dyes, and pyrylium dyes.

3. The radiation sensitive plate as claimed in claim 2, wherein the ring structure formed by $R_{10}$ and V taken together includes a heterocyclic oxygen.

4. The radiation sensitive plate as claimed in claim 2, wherein the ring structure formed by $R_{10}$ and V taken together includes a second carbonyl.

5. A radiation sensitive plate as claimed in claim 1, wherein the perester compound is selected from the group consisting of:
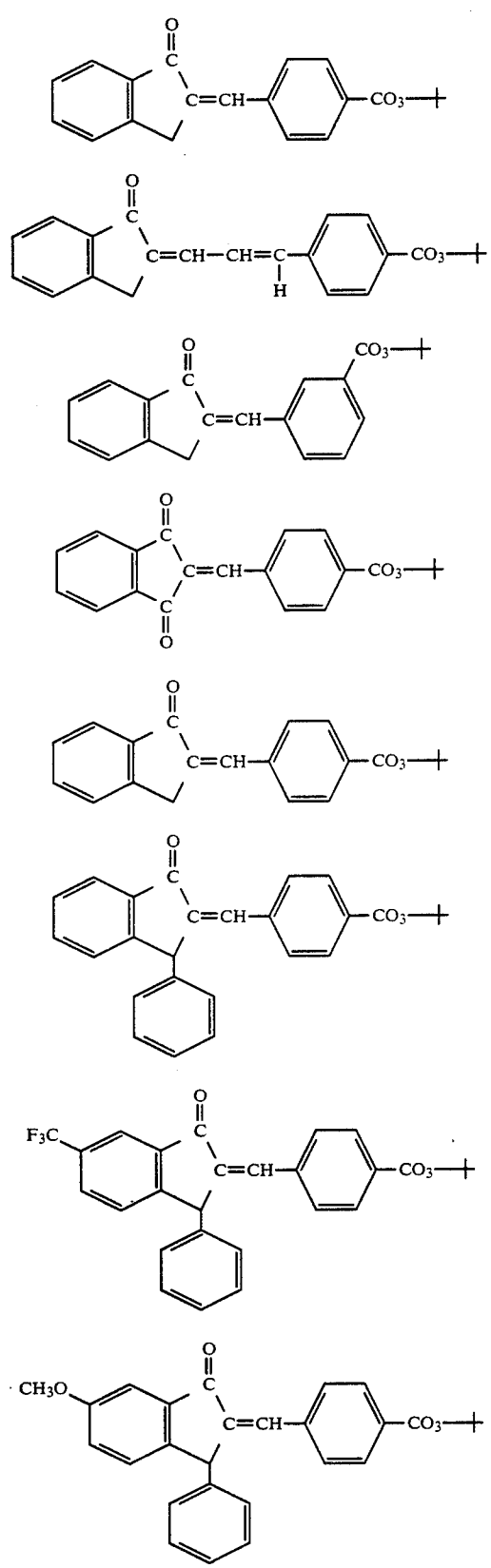
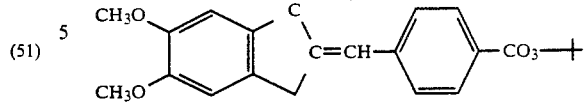
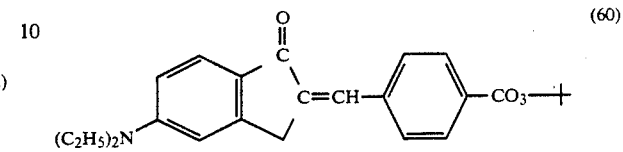
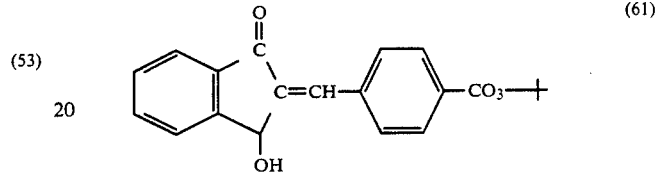
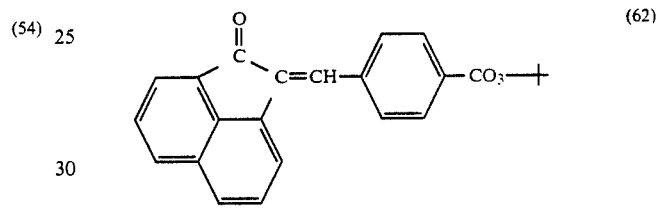
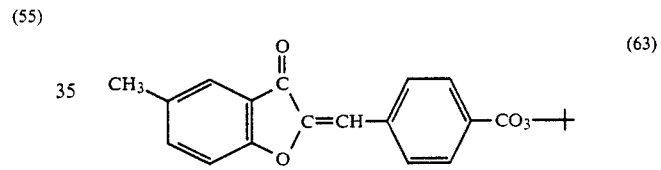
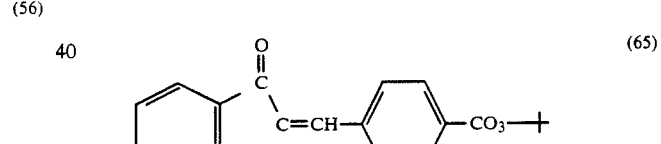
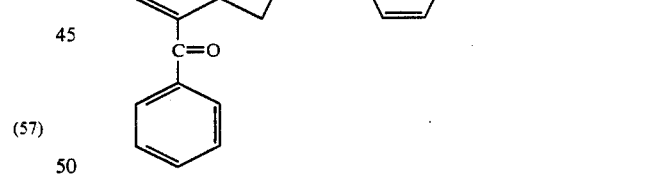
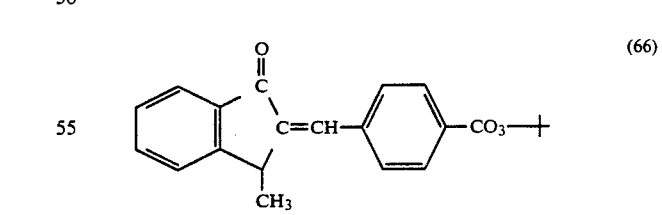
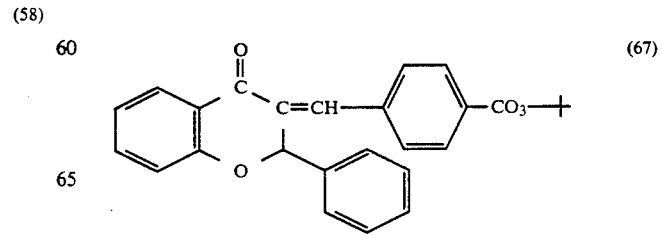

-continued

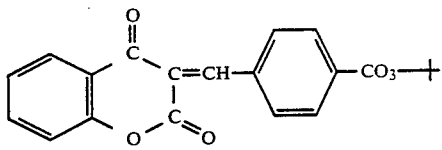
(68)

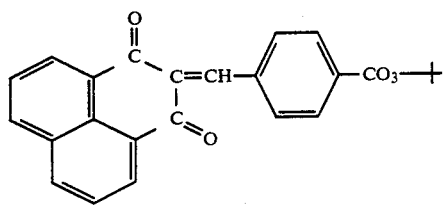
(69)

-continued

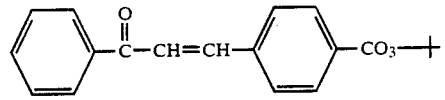
(82)

6. The radiation sensitive plate as claimed in claim 5, wherein the optical sensitizer is selected from the group consisting of coumarins, bis-coumarins, α,β-unsaturated ketones, methine dyes, and pyrylium dyes.

7. A radiation sensitive plate comprising a substrate coated with a photopolymerizable composition comprising (i) a dimethacrylate ester of a diglycidyl ether of bisphenol A, (ii) a perester having the formula

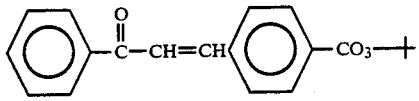

and (iii) an optical sensitizer.

8. The radiation sensitive plate as claimed in claim 7, wherein the optical sensitizer is selected from the group consisting of coumarins, bis-coumarins, α,β-unsaturated ketones, methine dyes, and pyrylium dyes.

* * * * *

UNITED STATES PATENT AND TRADEMARK OFFICE
CERTIFICATE OF CORRECTION

PATENT NO. : 5,130,227
DATED : July 14, 1992
INVENTOR(S) : Radiation Sensitive Plates It is certified that error appears in the above-identified patent and that said Letters Patent is hereby corrected as shown below:

```
Column 4 between lines 25 and 30 and before the formula
   insert -(1)-
Column 5, line 19 change "(21)" to -(2)-
Line 62 change "51" to -51-
Line 68 change "65" to -65-
Column 9, line 3 change "NO.2006" to -NO.2006775.-
Line 4 cancel "4775.1"
```

Signed and Sealed this

Eleventh Day of January, 1994

Attest:

BRUCE LEHMAN

*Attesting Officer*     *Commissioner of Patents and Trademarks*